US005785992A

United States Patent [19]
Ansell et al.

[11] Patent Number: 5,785,992
[45] Date of Patent: Jul. 28, 1998

[54] COMPOSITIONS FOR THE INTRODUCTION OF POLYANIONIC MATERIALS INTO CELLS

[75] Inventors: Steven Michial Ansell; Barbara Mui; Michael Hope, all of Vancouver, Canada

[73] Assignee: Inex Pharmaceuticals Corp., Canada

[21] Appl. No.: 536,584

[22] Filed: Sep. 29, 1995

[51] Int. Cl.[6] .................................................. A16K 9/127
[52] U.S. Cl. ............................................. 424/450; 935/54
[58] Field of Search ............................. 424/450; 935/54

[56] References Cited

U.S. PATENT DOCUMENTS

| | | |
|---|---|---|
| 4,394,372 | 7/1983 | Taylor ........................................ 424/85 |
| 4,897,355 | 1/1990 | Eppstein et al. . |
| 4,946,787 | 8/1990 | Eppstein . |
| 5,171,678 | 12/1992 | Behr et al. . |
| 5,234,767 | 8/1993 | Wallach . |
| 5,279,833 | 1/1994 | Rose . |
| 5,286,634 | 2/1994 | Stadler et al. . |

FOREIGN PATENT DOCUMENTS

| | | |
|---|---|---|
| 2552679 | 4/1985 | France . |
| 2147243 | 5/1985 | United Kingdom . |
| 2147263 | 5/1985 | United Kingdom ............ B01J 13/02 |
| WO 91/16024 | 10/1991 | WIPO . |
| WO 93/05162 | 3/1993 | WIPO . |

OTHER PUBLICATIONS

It. Biochemistry International 22 #2, p. 235 (1990).
Pinnaduwager BBA 985 p. 33 (1989).
Hawley–Nelson, et al., *focus*15(3) :73 (1993).
Stomatatos, et al., *Biochemistry* 27:3917–3925 (1988).
Zhu, N., et al., *Science* 261:209–211 (1993).
Leventis, et al., *Biochem. Biophys. Acta* 1023:124 (1990).
Chang, A.C.Y., et al., *Focus*, 10:68 (1988).
Hope, M.J., et al. *Biochimica et Biophysica Acta*,812:55–65 (1985).
Struck, D.K., et al.. *Biochemistry*, 20:4039 (1981) .
Woodle, M.C., et al.. *Biochimica et Biophysica Acta*, 1105:193–200 (1992).
Bennett, C.F., et al., *Molecular Pharmacology*, 41:1023–1033 (1992).
Wood, P.G., *Methods in Enzymology*, 149: 271–280 (1987).
Hyde, Stephen, C., et al., *Nature*, 362:250–255 (1993).
Brigham, Kenneth L., et al.. *American Journal of the Medical Sciences*, 278(4) :278–281 (1989).
Behr, et al.. *Proc. Natl. Acad. Sci. USA*, 86:6982–6986 (Sep. 1989).
Stewart, M.J., et al., *Human Gene Therapy*, 3:267–275 (1992).
Nicolau, C., *Methods in Enzymology*, 149:157–184 (1987).
Felgner, P.L., et al., *Proc. Natl. Acad. Sci., USA*, 84:7413–7417 (Nov. 1987).
Gao, X., et al., *Biochemical an Biophysical Research Communications*, 200(3) ;1201–1206 (May 16, 1994).
Pickering, J. G., et al.. *Circulation*, 89(1) :13–21 (Jan. 1994).
Kaneda, Y., et al., *Methods in Enzymology*, 221:317–327 (1993).

(List continued on next page.)

*Primary Examiner*—Gollamudi S. Kishore
*Attorney, Agent, or Firm*—Townsend and Townsend and Crew LLP

[57] ABSTRACT

The present invention provides compositions and methods which are useful for the introduction of polyanionic materials into cells. The compositions are mixtures of cationic compounds and neutral lipids which are typically formulated as liposomes. The cationic compounds are quaternary ammonium compounds wherein the nitrogen has two attached long chain alkyl groups, at least one of which is unsaturated. The methods for transfecting cells involve (a) contacting the polyanionic materials with the compositions above to form a polyanionic material-liposome complex, and (b) contacting the complex with the cells to be transfected.

6 Claims, 6 Drawing Sheets

OTHER PUBLICATIONS

Thierry, A.R., et al., *Nucleic Acids Research*, 20(21):5691–5698.

Keren-Zur, M., et al., *Biochimica et Biophysica Acta*, 983:253–258 (1989).

Nicolau, C., et al., *Methods in Enzymology*, 149:157–176 (1987).

Debs, R., et al., *Am. J. Respir. Cell Mol. Biol.*, 7:406–413 (1992).

Brigham, K.L., et al., *Am. J. Respir. Cell Mol. Biol.*, 8:209–213 (1993).

Canonico, A.E., et al., *Am. J. Respir. Cell Mol. Biol.*, 10:24–29 (1994).

Mack, K.D., et al., *Am. J. Medical Sciences*, 307 (2):138–143 (Feb. 1994).

Farhood, H., et al., *Annals New York Academy of Sciences*, 716:23–35 (1994).

Ito et al., *Synthetic Cationic Ampliphiles for Liposome–Mediated DNA Transfection:*, Biochemistry International, 22:No. 2, p. 235 (1990).

Pinnaduwage et al., "Use of a quaternary ammonium detergent in liposome mediated DNA transfection of mouse L-cells", *Biophysica Acta*, 985 p. 33–37 (1989).

Philip, R., "Cationic Liposome–Mediated Transfection of Immune Effector Cells," *J. of Liposome Research*, 391):71–84 (1993).

Philip, R., et al. (1993) "Cationic Lipsome–Mediated Transfection of Immune Effector Cells", *Journal of Liposome Research*, 3(1):71–84.

COMPOSITIONS FOR THE INTRODUCTION OF POLYANIONIC MATERIALS INTO CELLS

BACKGROUND OF THE INVENTION

Gene therapy is an area of current interest which involves the introduction of genetic material into a cell to facilitate expression of a deficient protein. There are currently five major methods by which this is accomplished, namely: (i) calcium phosphate precipitation, (ii) DEAE-dextran complexes, (iii) electroporation, (iv) cationic lipid complexes and (v) reconstituted viruses or virosomes (see Chang, et al., *Focus* 10:88 (1988)). Cationic lipid complexes are presently the most effective generally used means of effecting transfection.

A number of different formulations incorporating cationic lipids are commercially available, namely (i) LIPOFECTIN® (which uses 1,2-dioleyloxy-3-(N,N,N-trimethylamino)propane chloride, or DOTMA, see Eppstein, et al., U.S. Pat. No. 4,897,355); LIPOFECTAMINE® (uses DOSPA, see Hawley-Nelson, et al., *Focus* 15(3):73 (1993)); and LIPOFECTACE® (uses N,N-distearyl-N,N-dimethylammonium bromide, or DDAB, see Rose, U.S. Pat. No. 5,279,833). Other researchers have reported alternative cationic lipids that work in essentially the same manner but with different efficiencies, for example 1,2-dioleoyloxy-3-(N,N,N-trimethylamino)propane chloride, or DOTAP, see Stomatatos, et al., *Biochemistry* 27:3917–3925 (1988)); glycerol based lipids (see Leventis, et al., *Biochem. Biophys. Acta* 1023:124 (1990); lipopolyamines (see, Behr, et al., U.S. Pat. No. 5,171,678) and cholesterol based lipids (see Epand, et al., WO 93/05162).

Others have noted that DOTMA and related compounds are significantly more active in transfection assays than their saturated analogues (see, Felgner, et al., WO91/16024). However, both DOTMA and DOSPA based formulations, despite being the most efficient of the cationic lipids in effecting transfection, are prohibitively expensive. DDAB on the other hand is inexpensive and readily available from chemical suppliers but is less effective than DOTMA in most cell lines.

What is needed in the art are new compositions and methods which are both more effective at transfection and more affordable. Surprisingly, the present invention provides such compositions and methods.

SUMMARY OF THE INVENTION

The present invention provides compositions and methods which are useful for the introduction of polyanionic materials into cells. The compositions are mixtures of cationic compounds and neutral lipids which are typically formulated as liposomes. The cationic compounds are quaternary ammonium compounds wherein the nitrogen has two attached long chain alkyl groups, at least one of which is unsaturated. The methods for transfecting cells involve (a) contacting the polyanionic materials with a liposomal formulation of the above compositions to generate a complex, and (b) contacting the complex with the cells to be transfected.

DETAILED DESCRPITION OF THE INVETION

Abbreviations and Definitions

Figure 1:
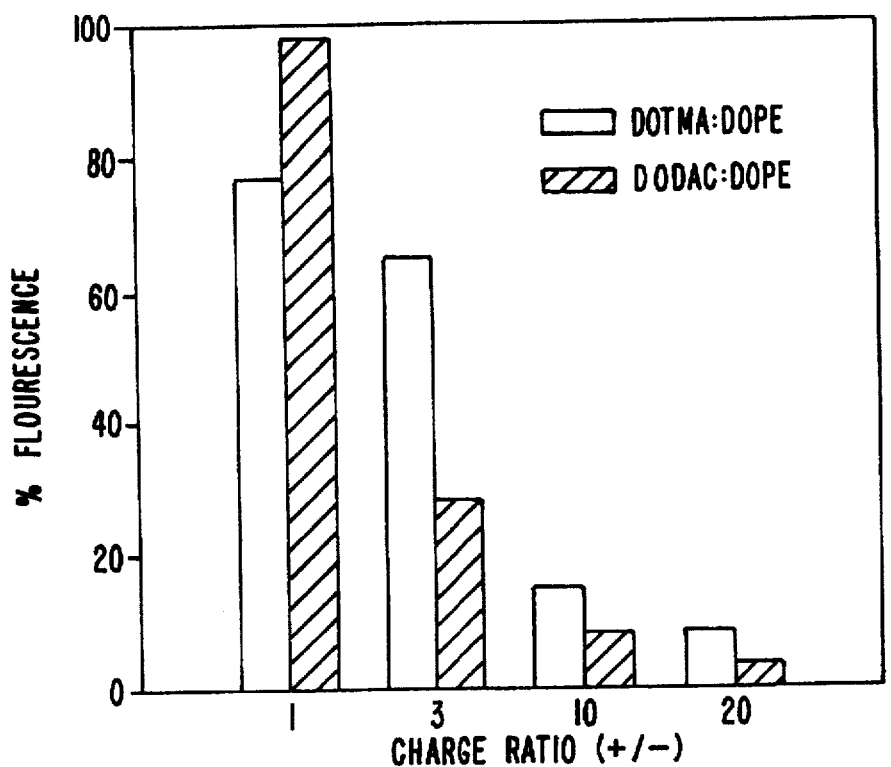
FIG. 1 illustrates the fusion of DOTMA:DOPE and DODAC:DOPE vesicles induced by plasmid DNA.

The following abbreviations are used herein: BHK, baby hamster kidney; RBC, red blood cells; DDAB, N,N-distearyl-N,N-dimethylammonium bromide; DODAC, N,N-dioleyl-N,N-dimethylammonium chloride; DOPE, 1,2-sn-dioleoylphoshatidylethanolamine; DOSPA, 2,3-dioleyloxy-N-(2(sperminecarboxamido)ethyl)-N,N-dimethyl-1-propanaminium trifluoroacetate; DOTAP, 1,2-dioleoyloxy-3-(N,N,N-trimethylamino)propane chloride; DOTMA, 1,2-dioleyloxy-3-(N,N,N-trimethylamino)propanechloride; OSDAC, N-oleyl-N-stearyl-N,N-dimethylammonium chloride; RT, room temperature; HEPES, 4-(2-hydroxyethyl)-1-piperazineethanesulfonic acid; FBS, fetal bovine serum; DMEM, Dulbecco's modified Eagle's medium; PEG-Cer-$C_{14}$, 1-O-(2'-(ω-methoxypolyethyleneglycol)succinoyl)-2-N-myristoyl-sphingosine; PEG-Cer-$C_{20}$, 1-O-(2'-(ω-methoxypolyethyleneglycol)succinoyl)-2-N-arachidoyl-sphingosine; PBS, phosphate-buffered saline; THF, tetrahydrofuran; EGTA, ethylenebis(oxyethylenenitrilo)-tetraacetic acid; SF-DMEM, serum-free DMEM; and NP40, nonylphenoxypolyethoxyethanol.

As used herein, the term "alkyl" refers to a saturated hydrocarbon radical which may be straight-chain or branched-chain (for example, methyl, ethyl, propyl, isopropyl). Preferred alkyl groups for some substituents are lower alkyl groups containing 1 to 3 carbon atoms. For other alkyl group substituents, long chain alkyl groups containing from 16 to 20 carbon atoms are preferred. All numerical ranges in this specification and claims are intended to be inclusive of their upper and lower limits.

The term "acyl" refers to a radical produced from an organic acid by removal of the hydroxyl group. Examples of acyl radicals include acetyl, pentanoyl, palmitoyl, stearoyl, myristoyl, caproyl and oleoyl.

As used herein, the term "pharmaceutically acceptable anion" refers to anions of organic and inorganic acids which provide non-toxic salts in pharmaceutical preparations. Examples of such anions include chloride, bromide, sulfate, phosphate, acetate, benzoate, citrate, glutamate, and lactate. The preparation of pharmaceutically acceptable salts is described in Berge, et al., *J. Pharm. Sci.* 66:1–19 (1977), incorporated herein by reference.

As used herein, the term "polyanion" refers to materials having more than one anionic group. For example, polyanion is used to refer to nucleic acids, both DNA and RNA which are present in their polyanionic form having more than one anionic phosphodiester group along the nucleic acid backbone. The term "polyanion" also refers to those pharmaceutical agents which have more than one anionic group at neutral pH. Such pharmaceutical agents include peptides having multiple carboxylic acid functionalities present (i.e., Glu, Asp).

The term "neutral lipid" refers to any of a number of lipid species which exist in an uncharged or neutral zwitterionic form at physiological pH. Such lipids include, for example diacylphosphatidylcholine, diacylphosphatidylethanolamine, ceramide, sphingomyelin, cephalin, cardiolipin, and cerebrosides.

The terms "transfection" and "transformation" are used herein interchangeably, and refer to the introduction of polyanionic materials, particularly nucleic acids, into cells. The term "lipofection" refers to the introduction of such materials using liposome complexes. The polyanionic materials can be in the form of DNA or RNA which is linked to expression vectors to facilitate gene expression after entry into the cell. Thus the polyanionic material used in the present invention is meant to include DNA having coding sequences for structural proteins, receptors and hormones, as well as transcriptional and translational regulatory elements (i.e., promoters, enhancers, terminators and signal sequences) and vectors. Methods of incorporating particular nucleic acids into expression vectors are well known to those of skill in the art, but are described in detail in, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference. "Expression vectors", "cloning vectors", or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

DETAILED DESCRIPTION

The present invention provides compositions and methods for the introduction of polyanionic materials into cells. The compositions comprise a cationic compound of formula I and at least one neutral lipid.

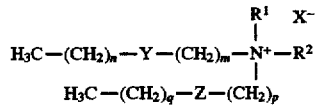

In formula I, $R^1$ and $R^2$ are each independently $C_1$ to $C_3$ alkyl. Y and Z are akyl or alkenyl chains and are each independently —$CH_2CH_2CH_2CH_2CH_2$—, —CH=CHCH$_2$CH$_2$CH$_2$—, —CH$_2$CH=CHCH$_2$CH$_2$—, —CH$_2$CH$_2$CH=CHCH$_2$—, —CH$_2$CH$_2$CH$_2$CH=CH—, —CH=CHCH=CHCH$_2$—, —CH=CHCH$_2$CH=CH—, or —CH$_2$CH=CHCH=CH—, with the proviso that Y and Z are not both —CH$_2$CH$_2$CH$_2$CH$_2$CH$_2$—. The letters n and q denote integers of from 3 to 7, while the letters m and p denote integers of from 4 to 9, with the proviso that the sums n+m and q+p are each integers of from 10 to 14. The symbol $X^-$ represents a pharmaceutically acceptable anion. In the above formula, the orientation of the double bond can be either cis or trans, however the cis isomers are generally preferred.

In one group of preferred embodiments, the cationic compounds are of formula I, wherein $R^1$ and $R^2$ are methyl and Y and Z are each independently —CH=CHCH$_2$CH$_2$CH$_2$—, —CH$_2$CH=CHCH$_2$CH$_2$—, —CH$_2$CH$_2$CH=CHCH$_2$— or —CH$_2$CH$_2$CH$_2$CH=CH—. In particularly preferred embodiments of the present invention, $R^1$ and $R^2$ are methyl; Y and Z are each —CH=CHCH$_2$CH$_2$CH$_2$—; n and q are both 7; and m and p are both 5. In the most preferred embodiment, the cationic compound is DODAC (N,N-dioleyl-N,N-dimethylammonium chloride). DODAC is a known compound that has been used extensively as an additive in detergents and shampoos. There is also a report of its use as a colipid in liposomal compositions with other detergents (see, Takahashi, et al., GB 2147243).

The neutral lipids which are part of the present compositions can be any of a variety of neutral lipids which are typically used in detergents, or for the formation of micelles or liposomes. Examples of neutral lipids which are useful in the present compositions are diacylphosphatidylcholine, diacylphosphatidylethanolamine, ceramide, sphingomyelin, cephalin, cardiolipin, and cerebrosides. In preferred embodiments, the present compositions will include one or more neutral lipids which are diacylphosphatidylcholine, diacylphosphatidylethanolamine, ceramide or sphingomyelin. The acyl groups in these neutral lipids are preferably acyl groups derived from fatty acids having $C_{10}$–$C_{24}$ carbon chains. More preferably the acyl groups are lauroyl, myristoyl, palmitoyl, stearoyl or oleoyl. In particularly preferred embodiments, the neutral lipid will be 1,2-sn-dioleoylphosphatidylethanolamine.

The anion, $X^{31}$, can similarly be any of a variety a pharmaceutically acceptable anions. These anions can be organic or inorganic, including for example, Br$^-$, Cl$^-$, F$^-$, I$^-$, sulfate, phosphate, acetate, nitrate, benzoate, citrate, glutamate, and lactate. In preferred embodiments, $X^-$ is Cl$^-$ or AcO$^-$.

In addition to the above components, the compositions of the present invention will also contain a pharmaceutically acceptable carrier. Pharmaceutically acceptable carriers well-known to those who are skilled in the art. The choice of carrier will be determined in part by the particular composition to be administered as well as by the particular method used to administer the composition. Preferably, the pharmaceutical carrier is water or saline.

In the compositions of the present invention, the ratio of cationic compound to neutral lipid will be within a range of from about 25:75 (cationic compound:neutral lipid) to 75:25 (cationic compound:neutral lipid), preferably about 50:50.

The cationic compounds which are used in the above compositions can be prepared by methods known to those of skill in the art using standard synthetic reactions (see March, *Advanced Organic Chemistry*, 4th Ed., Wiley-Interscience, NY, N.Y. (1992), incorporated herein by reference). For example, the synthesis of OSDAC can be carried out by first treating oleylamine with formaldehyde and sodium cyanoborohydride under conditions which result in the reductive alklation of the amine. This provides dimethyl oleylamine, which can then be alkylated with stearyl bromide to form the corresponding ammonium salt. Anion exchange results in the formation of OSDAC. Dimethyloleylamine can also be synthesized by treatment of oleyl bromide with a large excess of dimethylamine, and further derivatized as described above. For cationic compounds in which both fatty acid chains are unsaturated (i.e., DODAC), the following general procedure can be used. An unsaturated acid (i.e., oleic acid) can be converted to its corresponding acyl chloride with such reagents as oxalyl chloride, thionyl chloride, $PCl_3$ or $PCl_5$. The acyl chloride can be treated with an unsaturated amine (i.e., oleylamine) to provide the corresponding amide. Reduction of the amide with, for example, lithium aluminum hydride provides a secondary amine wherein both alkyl groups are unsaturated long chain alkyl groups. The secondary amine can then be treated with alkyl halides such as methyl iodide to provide a quaternary ammonium compound. Anion exchange can then be carried out to provide cationic compounds having the desired pharmaceutically acceptable anion. The alkylamine precursor can be synthesized in a similar manner. For example, treatment of an alkyl halide with a methanolic solution of ammonia in large excess will produce the required amine after purification. Alternatively, an acyl chloride, produced by treatment of the appropriate carboxylic acid with oxalyl chloride, can be reacted with ammonia to produce an amide. Reduction of the amide with $LiAlH_4$ will provide the required alkylamine.

In one group of embodiments, the pharmaceutical compositions of the present invention will be formulated as micelles or liposomes.

Micelles containing the cationic compounds and neutral lipids of the present invention can be prepared by methods which are well known to one of skill in the art. In addition to the micellar formulations of the present compositions, the present invention also provides micellar formulations which include other species such as lysophosphatidylcholine, lysophosphatidylethanolamine, lysophosphatidylserine, lysophosphatidylglycerol, phosphatidylethanolamine-polyoxyethylene conjugate, ceramide-polyoxyethylene conjugate or phosphatidic acid-polyoxyethylene conjugate. The polyoxyethylene conjugates which are used in the compositions of the present invention can be prepared by combining the conjugating group (i.e. phosphatidic acid or phosphatidylethanolamine) with an appropriately functionalized polyoxyethylene derivative. For example, phosphatidylethanolamine can be combined with ω-methoxypolyethyleneglycol succinate to provide a phosphatidylethanolamine-polyoxyethylene conjugate. See, Parr, et al., *Biochim. Biophys. Acta* 1195:21–30 (1994), incorporated herein by reference.

Liposomes can also be formed from the cationic compounds and neutral lipids of the present pharmaceutical compositions. The selection of neutral lipids is generally guided by consideration of, e.g., liposome size and stability of the liposomes in the bloodstream.

As noted above, the neutral lipid component in the liposomes is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In general, less saturated lipids are more easily sized, particularly when the liposomes must be sized below about 0.3 microns, for purposes of filter sterilization. In one group of embodiments, lipids containing saturated fatty acids with carbon chain lengths in the range of $C_{14}$ to $C_{22}$ are preferred. In another group of embodiments, lipids with mono or diunsaturated fatty acids with carbon chain lengths in the range of $C_{14}$ to $C_{22}$ are used. Additionally, lipids having mixtures of saturated and unsaturated fatty acid chains can be used. Liposomes useful in the present invention may also be composed of sphingomyelin or phospholipids with other head groups, such as serine and inositol. Still other liposomes useful in the present invention will include cholesterol, diglycerides, ceramides, phosphatidylethanolamine-polyoxyethylene conjugates, phosphatidic acid-polyoxyethylene conjugates, or polyethylene glycol-ceramide conjugates (e.g., PEG-Cer-$C_{14}$ or PEG-Cer-$C_{20}$). Methods used in sizing and filter-sterilizing liposomes are discussed below.

A variety of methods are available for preparing liposomes as described in, e.g., Szoka et al., *Ann. Rev. Biophys. Bioeng.* 9:467 (1980), U.S. Pat. Nos. 4,235,871, 4,501,728, 4,837,028, the text *Liposomes*, Marc J. Ostro, ed., Marcel Dekker, Inc., New York, 1983, Chapter 1, and Hope, et al., *Chem. Phys. Lip.* 40:89 (1986), all of which are incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

Following liposome preparation, the liposomes may be sized to achieve a desired size range and relatively narrow distribution of liposome sizes. A size range of about 0.2–0.4 microns allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present inventions, liposomes having a size of from about 0.05 microns to about 0.15 microns are preferred.

The compositions of the present invention are useful for the introduction of polyanionic materials into cells. Accordingly, the present invention also provides methods for introducing a polyanionic material into a cell. The methods are carried out in vitro by first contacting the polyanionic material with a composition of at least one neutral lipid and a cationic compound of formula I, to form a polyanionic material-liposome complex. After contacting the polyanionic material with the liposomal formulations to form a complex, the complex is then contacted with the cells for a period of time sufficient for transfection to occur.

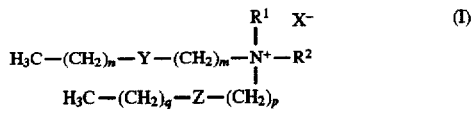

In formula I, the symbols $R^1$, $R^2$, Y, Z, n, m, p, q, and $X^-$ are as described above for the compositions of the present invention. In one group of preferred embodiments, the cationic compounds used in the present methods are of formula I, wherein $R^1$ and $R^2$ are methyl and Y and Z are each independently $—CH=CHCH_2CH_2CH_2—$, $—CH_2CH=CHCH_2CH_2—$, $—CH_2CH_2CH=CHCH_2—$ or $—CH_2CH_2CH_2CH=CH—$. In particularly preferred embodiments, $R^1$ and $R^2$ are methyl; Y and Z are each $—CH=CHCH_2CH_2CH_2—$; n and q are both 7; and m and p are both 5. More preferably, the cationic compound is DODAC (N,N-dioleyl-N,N-dimethylammonium chloride). Other preferred embodiments for the method of the present invention will encompass the preferred compositions discussed above.

As noted above, the polyanionic material is first contacted with a composition comprising neutral lipids and cationic compounds to provide a polyanionic material-liposome complex. The contact can be made either prior to liposome formation (from the neutral lipids and cationic compounds) or subsequent to an initial liposome formation. In a preferred embodiment, liposomes of neutral lipids and the cationic compounds are formed first, then brought into contact with the polyanionic materials. The polyanionic materials will typically bind to the surface of the liposome as a result of the ionic attraction between the negatively charged polyanionic material and the positively charged surface of the liposome. Typically, the contact between the polyanionic material and the liposome which results in formation of a complex will be carried out at temperatures of from about 15° C. to about 45° C., preferably about 25° C. The length of time required to complete the formation of a complex will depend on the temperature as well as the nature of the polyanionic material and the liposome itself. When contact temperatures of about 25° C. are used, the length of time to form a complex between a liposome and a nucleic acid will be about 15 minutes to about 2 hours, however in some instances longer times may be required. Alternatively, the polyanionic materials can be incorporated into the interior of the liposomes by methods used for loading conventional drugs which are known to those of skill in the art. One method for loading drugs into liposomes involves encapsulation and can be carried out by a variety of techniques.

In one encapsulation technique, the drug and liposome components are dissolved in an organic solvent in which all species are miscible and concentrated to a dry film. A buffer is then added to the dried film and liposomes are formed having the polyanionic material incorporated into the vesicle walls. Alternatively, the polyanionic material can be placed into a buffer and added to a dried film of only lipid components. In this manner, the polyanionic material will become encapsulated in the aqueous interior of the liposome. The buffer which is used in the formation of the liposomes can be any biologically compatible buffer solution of, for example, isotonic saline, phosphate buffered saline, or other low ionic strength buffers. Generally, the polyanionic material will be present in an amount of from about 0.01 ng/mL to about 50 mg/mL. The resulting liposomes with the polyanionic material incorporated in the aqueous interior or in the membrane are then optionally sized as described above.

In one group of preferred embodiments, the polyanionic material:liposome complexes will have charge ratios (±) of from about 0.5 to about 4.0. To achieve these charge ratios, the complexes are formed by preparing an aqueous liposome formulation of the cationic lipid and at least one neutral lipid in which the cationic lipid is present in from about 25% to about 75% of the total lipid concentration. After sizing the liposomes, as discussed above, an aqueous solution of the polyanionic material is treated with the liposome suspension. The resulting preparation is then diluted, preferably about 5-fold, with a biologically compatible buffer to provide a final concentration of 0.05 to 1.0 µg/mL of the polyanionic material:liposome complex having a charge ratio of from about 0.5 to about 4.0.

Following formation of a polyanionic material:liposome complex, the complex is contacted with the cells to be transfected. Liposomes can be adsorbed to almost any cell type. Once adsorbed, the liposomes (including the complexes previously described) can either be endocytosed by a portion of the cells, exchange lipids with cell membranes, or fuse with the cells. Transfer or incorporation of the polyanionic portion of the complex can take place via any one of these pathways. In particular, when fusion takes place, the liposomal membrane is integrated into the cell membrane and the contents of the liposome combine with the intracellular fluid. Contact between the cells and the polyanionic material-liposome complex, when carried out in vitro, will take place in a biologically compatible medium. The concentration of lipid can vary widely depending on the particular application, but is generally between about 1 µmol and about 10 mmol. Treatment of the cells with the polyanionic material:liposome complex will generally be carried out at physiological temperatures (about 37° C.) for periods of time of from about 1 to 6 hours, preferably of from about 2 to 4 hours. For in vitro applications, the delivery of polyanionic materials can be to any cell grown in culture, whether of plant or animal origin, vertebrate or invertebrate, and of any tissue or type. In preferred embodiments, the cells will be animal cells, more preferably mammalian cells, and most preferably human cells.

In one group of preferred embodiments, the polyanionic material:liposome complex is added to 60–80% confluent plated cells having a cell density of from about $10^3$ to about $10^5$ cells/mL, more preferably about $2\times10^4$ cells/mL. The concentration of the complex added to the cells is preferably of from about 0.01 to 0.2 µg/mL, more preferably about 0.1 µg/mL.

Typical applications include using well known transfection procedures to provide intracellular delivery of DNA or mRNA sequences which code for therapeutically useful polypeptides. However, the compositions can also be used for the delivery of the expressed gene product or protein itself. In this manner, therapy is provided for genetic diseases by supplying deficient or absent gene products (i.e., for Duchenne's dystrophy, see Kunkel, et al., *Brit. Med. Bull.* 45(3):630–643 (1989), and for cystic fibrosis, see Goodfellow, *Nature* 341:102–103 (1989)). Other uses for the compositions of the present invention include introduction of antisense oligonucleotides in cells (see, Bennett, et al., *Mol. Pharm.* 41:1023–1033 (1992)).

Alternatively, the compositions of the present invention can also be used for the transfection of cells in vivo, using methods which are known to those of skill in the art. In particular, Zhu, et al., *Science* 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250–256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.* 298:278–281 (1989), incorporated herein by reference, describes the in vivo transfection of lungs of mice with a functioning prokaryotic gene encoding the intracellular enzyme, chloramphenicol acetyltransferase (CAT).

When the polyanionic materials used in the present method are nucleic acids, they may be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., *Tetrahedron Lett.*, 22:1859–1862 (1981); Matteucci, et al., *J. Am. Chem. Soc.*, 103:3185–3191 (1981); Caruthers, et al., *Genetic Engineering*, 4:1–17 (1982); Jones, chapter 2, Atkinson, et al., chapter 3, and Sproat, et al., chapter 4, in *Oligonucleotide Synthesis: A Practical Approach*, Gait (ed.), IRL Press, Washington D.C. (1984); Froehler, et al., *Tetrahedron Lett.*, 27:469–472 (1986); Froehler, et al., *Nucleic Acids Res.*, 14:5399–5407 (1986); Sinha, et al. *Tetrahedron Lett.*, 24:5843–5846 (1983); and Sinha, et al., *Nucl. Acids Res.*, 12:4539–4557 (1984) which are incorporated herein by reference.

The present invention is also useful for introducing other polyanionic materials into cells, particularly proteins. The introduction of exogenous or endogenous proteins into a cell can provide suitable therapy for an individual having cells which are unable to carry out translation of mRNA.

The following examples are offered solely for the purposes of illustration, and are intended neither to limit nor to define the invention.

EXAMPLES

Materials

Oleylamine was obtained from Fluka Chemical Company, St. Louis, Mo., USA, and was also synthesized by the method described below. 40% Formaldehyde solution was obtained from Fischer Scientific, Ottawa, Canada. Sodium cyanoborohydride, stearyl bromide, oleic acid, oxalyl chloride, lithium aluminum hydride, methyl iodide and N-(2-hydroxyethyl)piperazine-N'-2-ethanesulfonic acid (HEPES) were obtained from Sigma Chemical Company, St. Louis, Mo, USA. N-(7-nitrobenz-2-oxa-1,3-diazol-4-yl)dioleoylphosphatidyl-ethanolamine (NBD-PE), N-(lissamine rhodamine 8 sulfony)dioleoylphosphatidyl-ethanolamine (Rho-PE) and 1,2-sn-dioleoylphoshatidyethanolamine (DOPE) were obtained from Avanti Polar Lipids, Alabaster, Ala., USA. The Lipex Extruder was obtained from Lipex Biomembranes, Vancouver, Canada. The pCMVβ expression vector (β-gal) was obtained from Clonetech Laboratories, Inc., Palo Alto, Calif., USA. Silica gel was obtained from BDH, Canada. PEG-Cer-$C_{14}$, PEG-Cer-$C_{20}$ and other PEG-modified lipids can be prepared by the methods provided in Parr, et al., *Biochim. Biophys. Acta* 1195:21–30 (1994) and in co-pending application Ser. No. 08/486,214.

EXAMPLE 1

This example illustrates the preparation of oleylamine This synthesis was developed as commercial oleylamine is often contaminated with elaidylamine.

A solution of oleic acid (5 g) in benzene was treated with oxalyl chloride (1 mL) with stirring at room temperature for one hour. Solvent was then removed by distillation. The residue was dissolved in methylene chloride and concentrated aqueous ammonia was added. The resulting emulsion was stirred for 2 hr at room temperature. After removal of ammonia under vacuum, the solution was acidified with hydrochloric acid and extracted with methylene chloride. The organic extract was dried, filtered and concentrated under reduced pressure. The resulting residue was dissolved in diethylether and excess lithium aluminum hydride was slowly added as a powder with vigorous stirring. A gelatinous suspension formed and was stirred for an additional 4 hr. Methanol was then slowly added until hydrogen evolution ceased. Excess dilute hydrochloric acid was added until all of the solids had been dissolved and no further hydrogen evolution was observed. The mixture was then extracted with methylene chloride. The organic phase was washed with saturated brine and solvent was removed on a rotary evaporator. The residue was passed down a silica gel column (Merck Art. 9385, 20 g gel per g of reaction product) using 2% methanol in methylene chloride (by volume) until all of the impurities (oleyl alcohol and unreduced oleolyamide) had eluted. The methanol concentration was then increased in 2% increments per 250 mL of eluant until a concentration of 24% was reached. The column was then flushed with methanol. Removal of solvent from those fractions containing product provided 3 g of oleylamine with no evidence of elaidylamine in the $^1$H NMR spectrum.

EXAMPLE 2

This example illustrates the synthesis of N-stearyl-N-oleyl-N,N-dimethylammonium chloride (OSDAC)

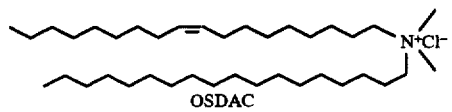

2.1 Synthesis of N,N-dimethyloleylamine

A solution of oleylamine (6.7 g) in acetonitrile (100 mL) and ethanol (50 mL) was treated with 40% aqueous formaldehyde (10 mL) and sodium cyanoborohydride (2.7 g) at room temperature for two hours. Acetic acid (5 mL) was slowly added and the solution stirred for an additional hour. The reaction mixture was then diluted with water, made basic with aqueous sodium hydroxide and extracted with methylene chloride, the organic fraction was dried over magnesium sulphate, filtered and the solvent was removed under vacuum. The residue was passed down a silica gel column (150 g) using 15% methanol in methylene chloride as the eluent, to provide a pale yellow oil (5 g).

2.2. Synthesis of OSDAC

A solution of N,N-dimethyloleylamine (1 g) and stearyl bromide (5.4 g) was dissolved in methylene chloride (50 mL) and treated with aqueous sodium hydroxide solution (5 mL of a 5M solution) at room temperature overnight with stirring. The reaction mixture was washed with water and then washed with dilute hydrochloric acid. The organic phase was washed with saturated sodium chloride solution (15×) and the solvent was removed. The residue was dissolved in methanolic hydrochloric acid and extracted from water and methylene chloride. This was repeated an additional three times. The organic solvent was then removed under vacuum and the residue passed down a silica gel column (150 g) using 5% methanol in methylene chloride as the eluent, to provide 0.6 g of OSDAC as a white powder after lyophilization from 10% methanol in benzene.

EXAMPLE 3

This example illustrates the synthesis of N,N-dioleyl-N,N-dimethyl-ammonium chloride (DODAC), using reductive amidation.

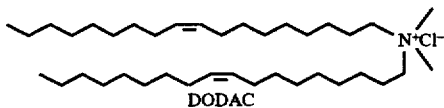

DODAC 3.1. Synthesis of N-oleyloleoylamide.

A solution of oleic acid (5 g) in benzene (50 mL) was treated with oxalyl chloride (2 mL) at room temperature for one hour. The solvent and excess oxalyl chloride was removed under vacuum and the residue was dissolved in benzene (20 mL). A solution of oleylamine (7 g) in benzene (10 mL) was slowly added, followed by triethylamine (3 mL). The reaction mixture was stirred at room temperature for one hour and then neutralized with excess dilute hydrochloric acid. The mixture was extracted with methylene chloride and the combined organic extracts were dried over magnesium sulphate, filtered and the solvent was removed. The residue was passed down a silica gel column (150 g) using 5% methanol in methylene chloride as the eluent, to provide N-oleyloleoylamide as a white solid.

3.2. Synthesis of dioleylamine.

A solution of N-oleyloleoylamide (prepared above) in THF (100 mL) was warmed to 40° C. Lithium aluminum hydride was slowly added until violent evolution of gas ceased. The reaction mixture was heated to reflux for one hour and then cooled to room temperature. Methanol (100 mL) was slowly added, followed by water (200 mL). Methylene chloride was added and the resultant suspension was stirred for fifteen minutes. The slurry was filtered and the precipitate was washed with ethanolmethylene chloride (50:50, 50 mL, 2×). The combined filtrates were extracted with methylene chloride. The organic fraction was dried over magnesium sulphate, filtered and the solvent was removed under vacuum. The residue was passed down a silica gel column (150 g) using 5% methanol in methylene chloride as the eluent, to provide dioleylamine as a pale yellow oil.

3.3. Synthesis of N,N-dioleyl-N,N-dimethylammonium chloride.

A solution of dioleylamine, prepared above, in chloroform (50 mL) was treated with methyl iodide (10 mL) at room temperature for one hour. Aqueous sodium hydroxide (1 mL of a 5M solution) and methyl iodide (5 mL) were then added and the mixture was stirred for an additional hour. The organic solvent was removed under vacuum and the resultant slurry was neutralized with dilute hydrochloric acid. Water was added and the reaction mixture was extracted with methylene chloride. The organic phase was washed with saturated sodium chloride solution (15×), after which the solvent was removed from the organic phase under vacuum. The residue was dissolved in a solution of concentrated hydrochloric acid in wet ethanol, diluted with water and extracted with methylene chloride. This process was repeated an additional three times. The product, after removal of solvent, was passed down a silica gel column (150 g) using methanol in methylene chloride as the eluent (increasing the amount of methanol from 5% to 32%, by volume). Pure fractions were combined and the solvent was removed, to provide N,N-dioleyl-N,N-dimethylammonium chloride (5 g) either as a white waxy solid or a colorless oil which solidified on standing. The DODAC can then be packaged by lyophilization from 10% methanol in benzene, as a white sticky powder.

EXAMPLE 4

This example illustrates the synthesis of N,N-dioleyl-N,N-dimethyl-ammonium chloride (DODAC) by an alkylation route.

A solution of dimethylamine was prepared by bubbling anhydrous dimethylamine gas through dry methanol (200 mL) for 30 min. Oleyl bromide (5 g) was added and the solution was stirred at room temperature in the dark for 16 hours. The solvent was removed on a rotary evaporator and residual dimethylamine was removed by two additions of anhydrous ethanol (50 mL) followed by removal of the solvent on a rotary evaporator. Oleyl bromide (10 g) was added to the residue and the mixture was dissolved in chloroform (40 mL). Sodium hydroxide solution (10 mL of 1N) was added and the resulting solution was gently refluxed for 16 hours in the dark.

The organic solvent was removed on a rotovap and the residue was dissolved in ethanol (50 mL). Concentrated HCl (33%, 10 mL) was added, followed by distilled water (100 mL). The resulting emulsion was extracted with chloroform (3×50 mL, followed by 2×25 mL). The extracts were combined and resubjected to the wash/extraction procedure for another five cycles. The organic solvent was then removed on a rotary evaporator and the residue was suspended in saturated sodium chloride solution. The solution was extracted with chloroform (3×50 mL, followed by 2×25 mL). This process was repeated. The organic solvent was removed on a rotary evaporator and the residue was dried by two additions of dry ethanol followed by removal of the solvent on a rotary evaporator. The residue was purified using silica gel chromatography (200 g silica gel) and a gradient elution of methanol in chloroform (from 2% to 12% methanol). Fractions containing pure DODAC were combined and the solvent was removed to provide 7 g of a colorless gum. Lyophilization from 10% methanol in benzene provided DODAC as a colorless sticky powder.

EXAMPLE 5

This example illustrates the fusogenicity of cationic vesicle/DNA complexes with biomembranes.

5.1. Vesicle-vesicle fusion.

The vesicles used for these experiments were made by the extrusion procedure as previously described (see Hope, et al., *Biochim. Biophys. Acta* 812:55 (1985), incorporated herein by reference). Briefly, the cationic lipids mixtures, consisting of equal molar ratios of cationic lipid and DOPE, were dried down from chloroform under a stream of nitrogen gas. The residual solvent was removed under vacuum for two hours. The dry lipid film was hydrated in distilled water and the resulting multilamellar vesicle (MLV) suspension was freeze thawed five times using liquid nitrogen and warm water cycles. Large unilamellar vesicles were then formed by forcing the MLV suspension through two stacked 100 nm pore sized filters using the Lipex extruder.

Vesicle fusion was monitored using resonance energy transfer as previously described in Struck, et al., *Biochemistry* 20:4093 (1981), incorporated herein by reference. Briefly, unlabelled vesicles were mixed 10:1 with similar vesicles containing 0.5 mole % each of Rho-PE (N-(lissamine rhodamine B sulfonyl)dioleoylphosphatidylethanolamine) and NBD-PE (N-(7-nitrobenz-2-oxa-1,3-diazol-4-yl)-dioleoylphosphatidylethanolamine) in 20 mM HEPES pH 7.4 buffer. The latter membrane fluorescent probe serves as the energy donor and the former as the energy acceptor. Fusion of labelled vesicles with unlabelled vesicles results in probe dilution. Thus, an increase in NBD-PE fluorescence due to a reduction of Rho-PE vesicles would be indicative of membrane fusion. A 7kB β-gal plasmid was used to induce fusion of the cationic vesicles. FIG. 1 shows the results obtained from fusion experiments of DOTMA:DOPE and DODAC:DOPE with plasmid DNA. The charge ratios were calculated based on an average nucleotide molecular weight of 325. As FIG. 1 indicates, both DOTMA:DOPE and DODAC:DOPE vesicles fuse to a similar extent at all charge ratios and show optimal fusogenicity at a charge ratio of 1, which corresponds to the optimal charge ratio for transfection for both species (see FIG. 4).

5.2. Lipid-DNA complex fusion with Red Blood Cell (RBC) ghosts.

Figure 2:
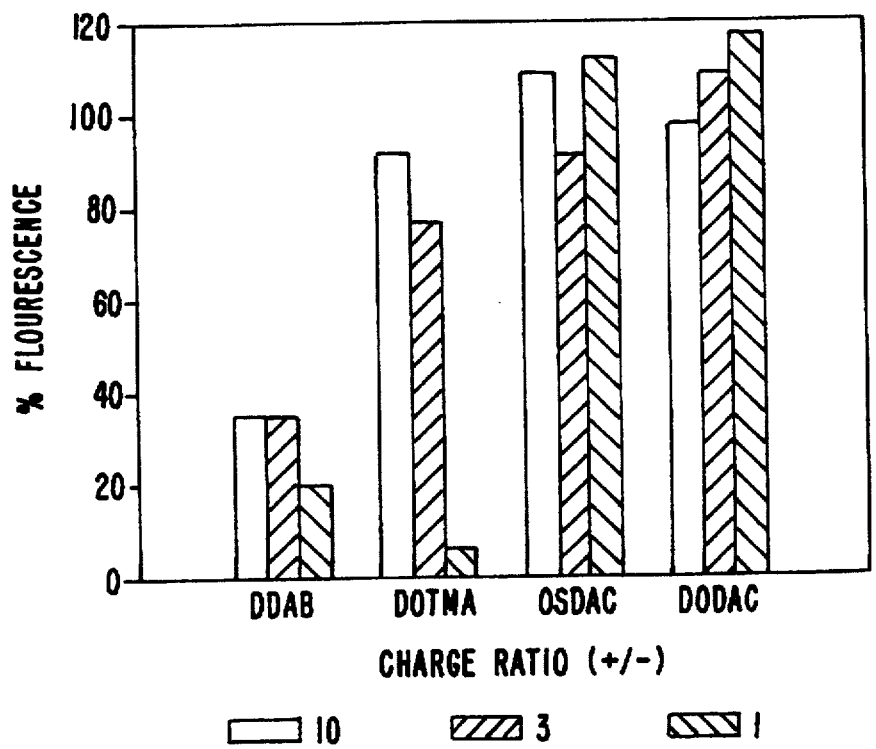
FIG. 2 illustrates the fusion of lipid/DNA complexes with RBC ghosts.

Cationic vesicles labelled with 0.5% each of Rho-PE and NBD-PE were mixed with a 7kB β-gal plasmid in 20 mM HEPES pH 7.4 buffer. The lipid-DNA complex was then added to a solution of RBC ghosts. Fusion with the ghost membrane would result in probe dilution and an increase in NBD fluorescence. RBC ghosts were prepared as previously described in the literature (see, Wood, *Methods in Enzymology*, 149:271–280 Academic Press (1987)). FIG. 2 shows the results of lipid/DNA complex-RBC ghost fusion experiments using three different charge ratios and four different cationic lipids (DDAB, DOTMA, OSDAC, and DODAC). As FIG. 2 illustrates, the unsaturated derivatives, DOTMA, DODAC and OSDAC, have superior fusion properties with respect to biological membranes than the saturated derivative, DDAB. In addition, DODAC and OSDAC show better fusogenic properties with RBC ghosts than DOTMA, which is the most commonly used commercial transfection lipid.

EXAMPLE 6

This example provides one procedure whereby BHK cells can be transfected using a β-gal plasmid and also provides a comparison of the relative transfection efficiencies DODAC-, DDAB-, DOTMA- and OSDAC-containing vesicles.

6.1 Preparation of cationic liposomes

Cationic liposomes were prepared from DOPE and DODAC, DDAB, DOTMA or OSDAC by the method described in Example 5. The cationic lipids were each mixed together with DOPE to form vesicles having charge ratios of 0.25, 0.5, 3 and 4 (for each of the four pairs of mixtures).

6.2 Transfection of BHK cells

A general lipofection protocol was carried out as follows:

On Day 1, BHK cells were plated at $10^4$ cells/well of a 24-well plate in 0.5 mL of media (5% FBS in DMEM). On the second day, lipid:DNA complexes were prepared in 24-well plates by first dispensing $H_2O$ into the wells and then adding the lipid. The DNA was prepared in $H_2O$ and then added to the wells, agitated to mix and incubated at room temperature for 30 minutes. During the incubation period the media was removed from the cells and the cells were washed in PBS. After washing, 750 μL of SF-DMEM was added.

The lipid:DNA complexes (200 μL) were added to the appropriate wells containing the BHK cells and the plate was agitated to mix, then incubated at 37° C. for 4 hours. The transfection media was then replaced with 0.5 mL of 5% FBS in DMEM. On day 3, the media was removed and the cells were stained following a standard procedure for the histochemical stain for β-galactosidase. On day 4, the stain was removed and the cells were washed with PBS, covered with 70% ethanol and counted.

6.3 Histochemical Staining For β-Galactosidase

The solutions required for histochemical staining include stock buffers, fixative, wash, and stain. These solutions were prepared and stored as follows:

1. Stock buffers were prepared as aqueous solutions using distilled, deionized water. Storage temperatures are as indicated. The solutions included: 47% glutaraldehyde, 4° C.; 1M $MgCl_2$, RT; 100 mM EGTA, pH 7.2, RT; 10% sodium deoxycholate, RT; 10% NP40, RT; 1M HEPES, 4° C.; 50 Mm $K_3Fe(CN)_6$, 4° C., stored in the dark for up to 3 months; 50 mM $K_4Fe(CN)_6$, 4° C., stored in the dark for up to 3 months; 5M NaCl, RT; and X-gal, a solid, was stored at −20° C.

2. The fixative solution had final concentrations of 0.2% glutaraldehyde, 2 mM $MgCl_2$ and 5 mM EGTA, and was prepared by combining 220 μL of 47% glutaraldehyde, 100 μL of $MgCl_2$ solution, and 2.5 mL of 100 mM EGTA at pH 7.2, and adjusting the total volume to 50 mL with PBS.

3. The wash solution was prepared by combining 100 μL of $MgCl_2$ solution, 500 μL of 10% sodium deoxycholate, and 100 μL of 10% NP40 and adjusting the total volume to 50 mL. This resulted in final concentrations of 2 mM $MgCl_2$, 0.1% sodium deoxycholate, and 0.02% NP40.

4. The stain was prepared by combining 2.2 mL of 1M HEPES, 3.0 mL of 50 mM $K_3Fe(CN)_6$, 3.0 mL of 50 mM $K_4Fe(CN)_6$, 150 μL of 5M NaCl, 65 μL of 1M $MgCl_2$ and $H_2O$ to provide a total volume of 50 mL. The solution was warmed to 42° C. and 12.5 mg of X-gal in 100 μL DMF (0.4% final volume) was added and dissolved. Alternatively, the X-gal can be made in DMF at 125 μg/μL and stored at −20° C. in foil. The final concentrations of the species in solution were 44 mM HEPES, 3 mM $K_3Fe(CN)_6$, 3 mM $K_4Fe(CN)_6$, 15 mM NaCl, 1.3 mM $MgCl_2$, and 0.5 mg/mL X-gal.

Cells were stained as follows:

The cells were washed once with PBS. Fixative (5 mL) was added to each plate and the cells were incubated at RT for five minutes. The fixative was removed and the cells were washed twice (3 minutes each) with permeabilization solution. X-gal stain (500 μL per well) was added to the cells which were then incubated overnight at 37° C. in an atmosphere of carbon dioxide. The pH of all of the solutions was maintained at 7.5–8.0 to avoid background interference from endogenous β-galactosidase.

6.4 Results

Figure 3:
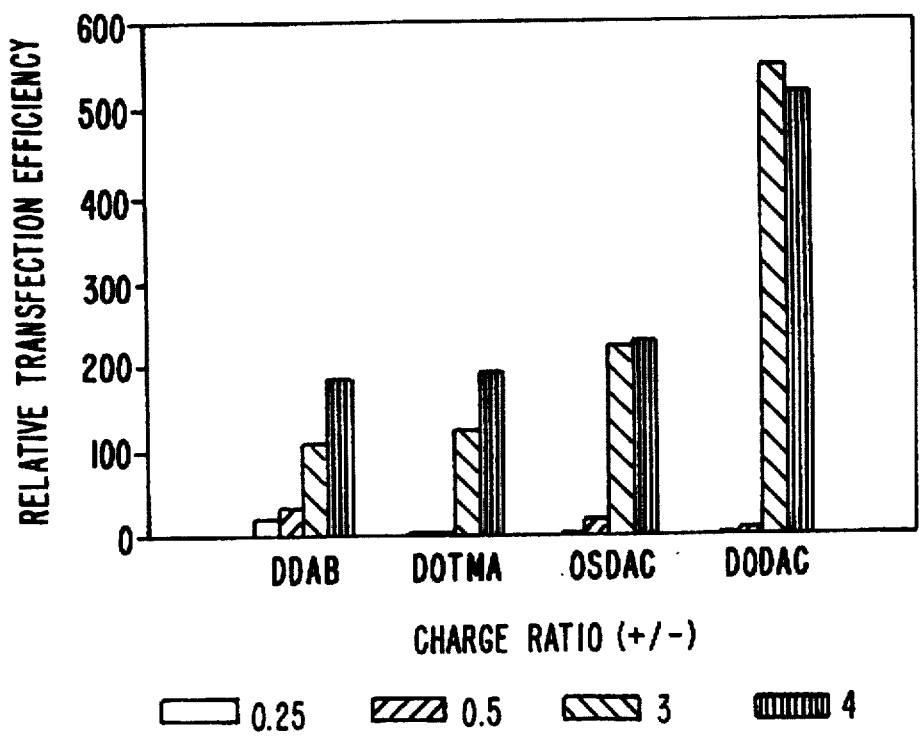
FIG. 3 illustrates a preliminary survey of the transfection abilities of cationic lipid vesicles formulated with 50 mole % DOPE.

FIG. 3 provides a survey of the relative transfection efficiencies of four lipids, DDAB, DOTMA, OSDAC and DODAC at four charge ratios (0.25, 0.5, 3 and 4). The relative transfection efficiency is the average number of transfected cells for 25 arbitrary areas on the cell plate. DODAC shows significantly better relative transfection efficiencies at charge ratios in excess of 1, whereas DDAB, DOTMA and OSDAC are all similar. All preparations have low transfection efficiencies below a charge ratio of 1. The comparison between DDAB and DODAC is particularly important as it demonstrates the effect of unsaturation on transfection efficiency.

Figure 4:
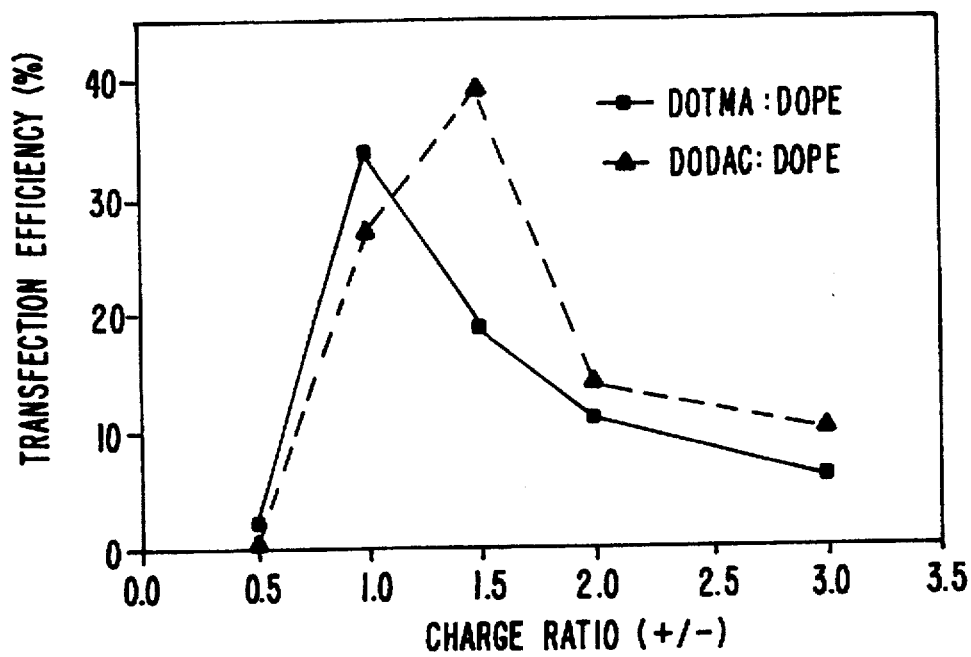
FIG. 4 illustrates the charge ratio titration of DOTMA:DOPE and DODAC:DOPE transfection efficiencies in BHK cells.

The transfection efficiency, expressed in terms of the number of transfected cells over the total number of cells, of DODAC and DOTMA at various charge ratios is shown in FIG. 4. Optimal transfection for both systems occurs for charge ratios between 1 and 2, and levels off at higher charge ratios. The transfection efficiency at charge ratios below 1 are markedly lower, consistent with the results presented in FIG. 3.

EXAMPLE 7

This example illustrates the use of various cationic liposome vesicles to provide transfection of cultured myoblasts.

Significant interest has developed in the use of genetically-altered myoblast therapy for the treatment of inherited diseases, such as Duchenne Muscular Dystrophy, or hemophilia A or B. This ex vivo approach takes advantage of the ability of myoblasts to fuse with myotubes when injected into skeletal tissue. In this manner, genetically altered myoblasts can be used to transfer corrective genes to muscle fibers. Viral vectors or naked DNA are the most commonly used vectors to transfect muscle cells. The strong immune responses resulting from the use of viral vectors limits their use. Naked DNA injections are very inefficient at transfecting muscle cells.

7.1 Cells and culture conditions

H9C2(2-1), a muscle cell line derived from rat fetal heart, was obtained from ATCC. The cells were propagated in a-Minimal Essential Medium (α-MEM), supplemented with 10% fetal bovine serum (FBS) and 10 mg/mL gentamicin (normal growth medium). Cultures were maintained at 37° C. in an atmosphere of 5% $CO_2$. Transfections were performed in 24 well plates (2 $cm^2$ surface area). Cells were transfected at three different stages: 50% confluent myoblasts, 100% confluent myoblasts and differentiated myotubes. Myoblasts were plated the day before the transfection at about $3 \times 10^4$ and $7 \times 10^4$ cells/$cm^2$ for sub-confluent and confluent densities, respectively. Myotube formation was induced by replacing the normal growth medium with fusion medium (α-MEM containing 2% FBS and 10 mg/mL gentamicin) when cells were confluent. After 4 d in fusion medium, the myotubes were transfected.

7.2 Plasmid pCMVβ (from Clonetech) is a plasmid that contains the β-galactosidase gene driven by the CMV promoter and SV40 enhancer. pCMVβ was grown following standard techniques and was purified by Qiagen Maxi columns (Qiagen, Chatworth, Calif., USA).

7.3 Cationic liposomes

Liposome formulations consisted of DODAC:DOPE (3:7 mol/mol) or DODAC:DOPE (3:7 mol/mol) containing 2 or 5 mol % PEG-Cer-$C_{14}$. Commercially available LIPOFECTAMINE® (from Gibco, polycationic liposomes containing DOSPA (2,3-dioleyloxy-N-(2-(sperminecarboxamido)ethyl)-N,N-dimethyl-1-propanaminiumtrifluoroacetate) and DOPE in a 3:1 molar ratio), was used for comparison.

7.4 Transfections

Plasmid DNA (290 ng) in 15 µL of 20 mM Hepes, pH 7.4, buffer was added to 10 µL of serum free medium (α-MEM). The resulting mixture was then added to 20 µL of serum free medium containing the desired amount of cationic liposomes. The mixture was incubated for 45 min at room temperature and then diluted to 200 βL total volume with serum free medium or with α-MEM containing 12.5% or 2.5% FBS for myoblasts or myotubes, respectively. Cells growing in a 24 well tissue culture plate were rinsed twice with serum free medium and then incubated for 5 h in the presence of the transfection mixture. Following the 5 h incubation 200 µL of α-MEM containing twice the normal amount of FBS was added. After 24 h, the media was replaced with 500 µL of fresh media. After another 24 h, the cells were rinsed twice with phosphate buffered saline and then lysed with 100 µL of cell lysis buffer (from Promega, Madison, Wis., USA). The β-galactosidase activity was measured as described above. The Bradford protein assay (from Pierce, Rockford, Ill., USA) was used to estimate the protein concentration of the lysates. The β-gal activity was normalized to the protein concentration of each sample.

7.5 Results

Figure 5A:
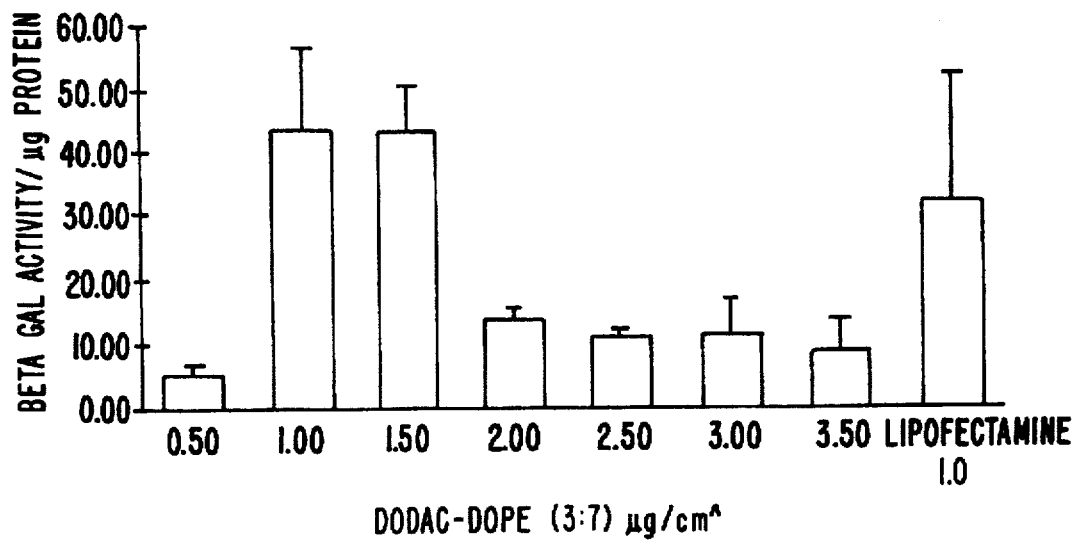
FIGS. 5A and B illustrate the transfection efficiencies of DODAC:DOPE complexes with 50% confluent H9C2 myoblasts in the absence (FIG. 5A) and presence (FIG. 5B) of serum.
Figure 5B:
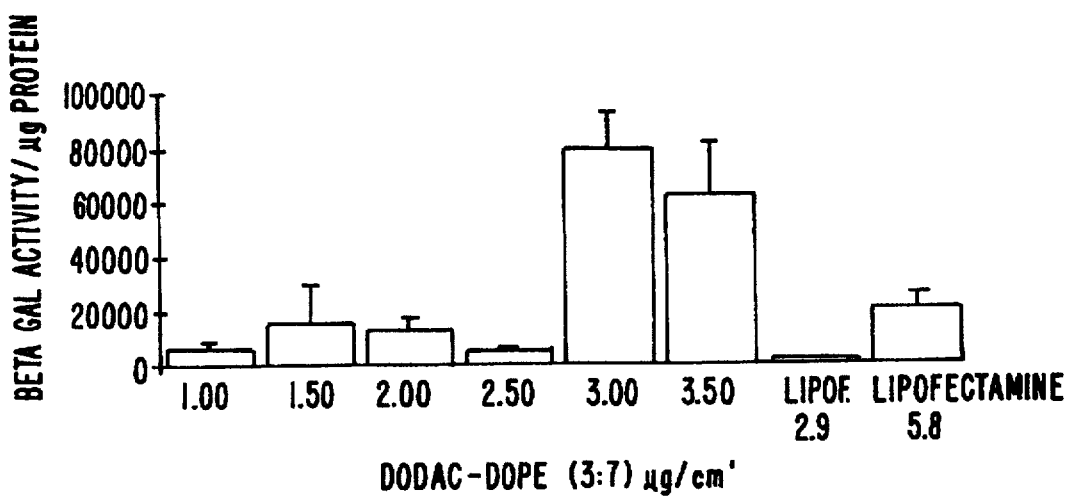
Figure 6A:
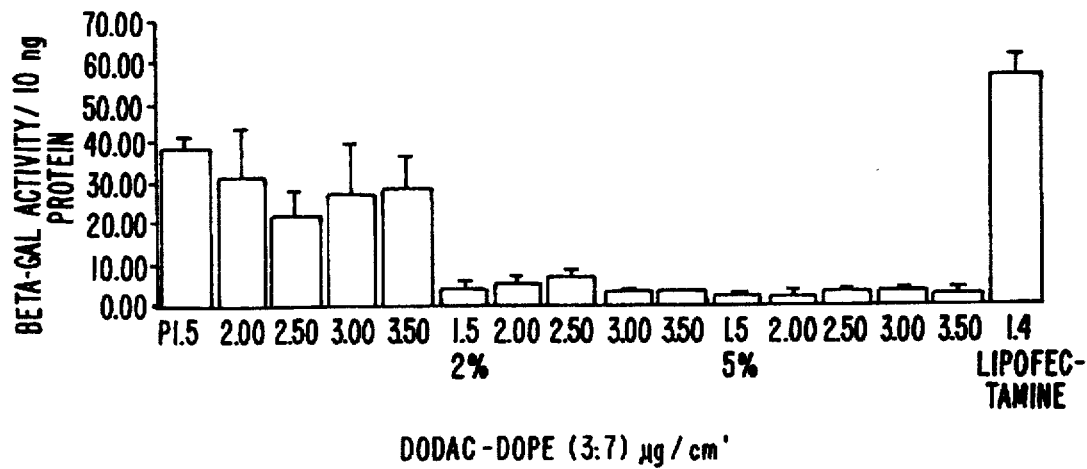
FIGS. 6A and B illustrate the transfection efficiencies of DODAC:DOPE complexes with 100% confluent H9C2 myoblasts in the absence (FIG. 6A) and presence (FIG. 6B) of serum.
Figure 6B:
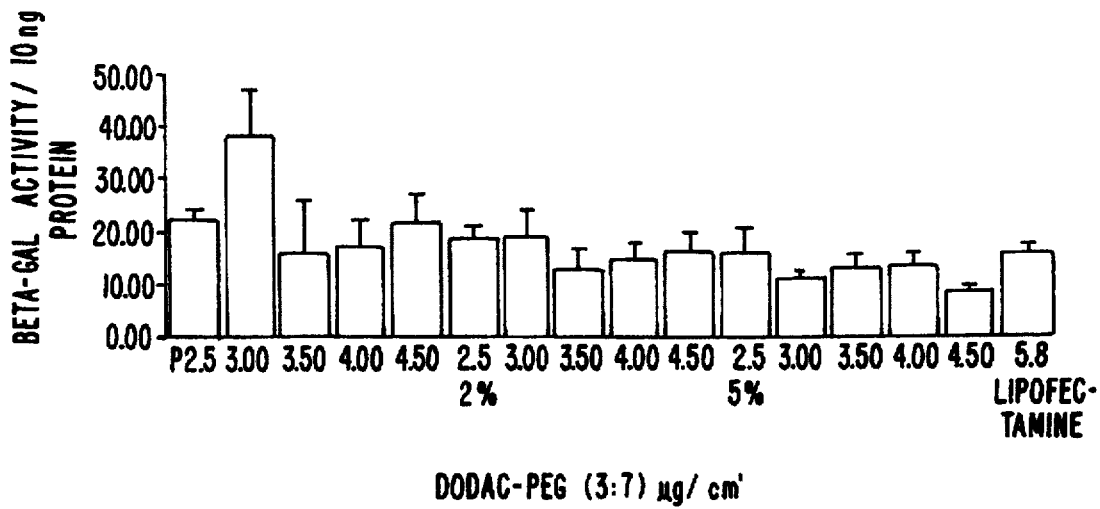
Figure 7A:
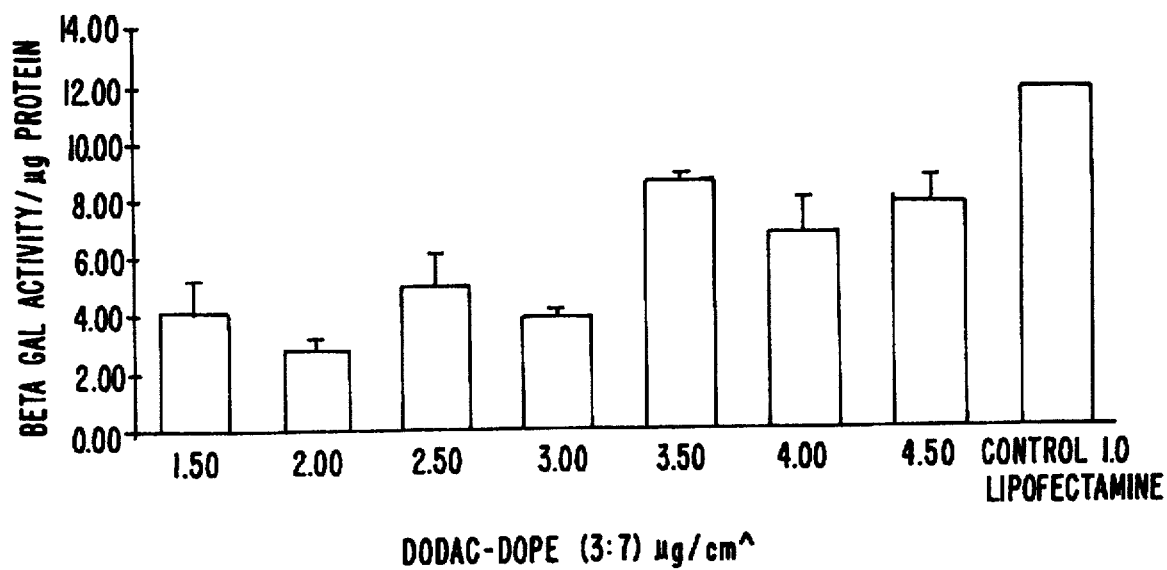
FIGS. 7A anbd B illustrate the transfection efficiencies of DODAC:DOPE complexes with H9C2 myotubes in the absence (FIG. 7A) and presence (FIG. 7B) of serum.
Figure 7B:
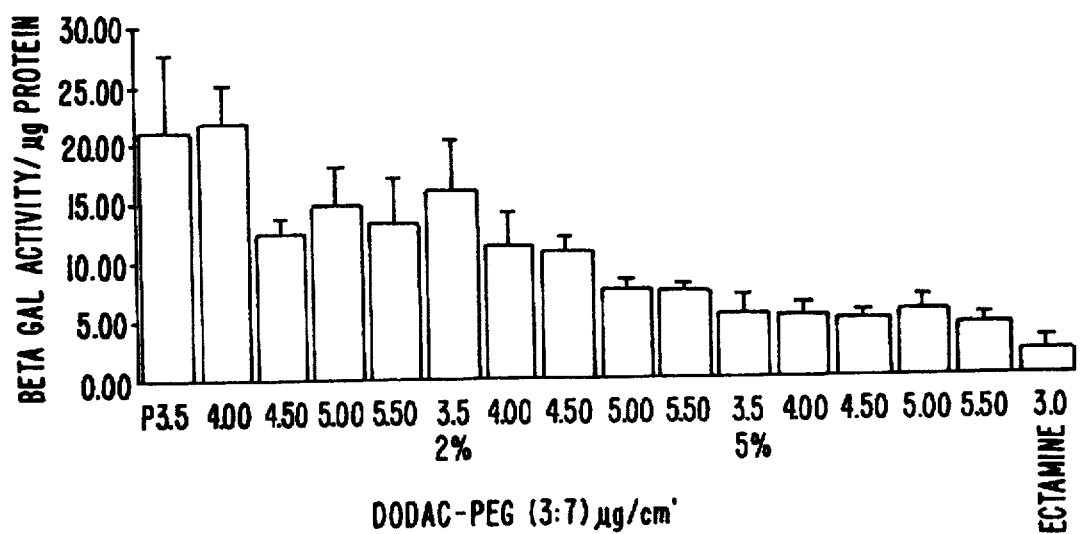

As shown in FIGS. 5–7, DODAC-containing liposomes are capable of transfecting H9C2 myoblasts and myotubes. Transfection is dependent on the amount of cationic liposome added to the cells, as well as to the state of confluency and differentiation. Furthermore, transfections can be done in the presence of serum. Additionally, when the transfections are done in the presence of serum, DODAC-containing liposomes are more efficient at transfecting myoblasts and myotubes than the optimal amounts of commercially available LIPOFECTAMINE®. Until now, LIPOFECTAMINE® has been the only cationic liposome formulation recognized to have the ability to transfect cells in the presence of serum. These findings, especially the ability to transfect myotubes in the presence of serum, indicate that the DODAC-containing systems can deliver genes to muscle cells directly in vivo.

EXAMPLE 8

This example illustrates the use of various cationic liposome vesicles to transfect lymphocyte and macrophage cell types in vitro.

Strategies for the treatment of viral infections, such as HIV-1 (AIDS), are increasingly focused on gene therapy approaches due to lack of drugs or vaccines that show long-term efficacy in vivo. A poly TAR/anti-Tat anti-HIV-I gene system has been developed that functions to inhibit HIV-I replication (see, Lisziewicz, et al., J. Virol. 69:206–212 (1995)). Nevertheless, delivery of the gene to the target site remains a problem. The major cellular targets are $CD4^+$ T lymphocytes and macrophages since these are the cells that harbor the virus. This example illustrates the ability of cationic liposomes to deliver genes to these cell types in culture.

8.1 Animals

Inbred C57BL/6 female mice (from Jackson Laboratories, Bar Harbor, Me., USA) were used in this study. Mice were purchased at 5 weeks of age and housed (under no stress condition) 5 per cage in a colony room were a day-night (12 hr) cycle was maintained through artificial illumination. The animals received free access to both food and water throughout the experiment and at least a one week acclimation period prior to the experimental manipulations.

8.2 Formation of transfection complexes

DODAC:DOPE (1:1 mol/mol) liposomes in water (1 mM concentration) were prepared by the extrusion procedure, as described above. pCMVβ (from In Vitrogen, San Diego, Calif., USA) was purified from *E. coli* lysates using the Qiagen method (Qiagen, Chatworth, Calif., USA).

For the formation of the transfection complexes, 20 μg pCMVβ (62 nmol phosphate) in a volume of 500 μL water was added to 186 nmol DODAC:DOPE in 500 μL water. This ratio of lipid:DNA results in a charge ratio of 1.5 (±). The suspension was incubated for 20–30 min at room temp.

8.3 Mitogen stimulation assay

Seven week old mice were sacrificed by cervical dislocation. The spleen, thymus and bone marrow were removed and single cell suspensions were prepared. Cellularity of these lymphoid organs was assessed by trypan blue exclusion test. Cell suspensions were adjusted to the desired concentration ($5 \times 10^6$/mL for spleen; $1 \times 10^7$/mL for thymus, and $2 \times 10^6$/mL for bone marrow) and were plated in 48 well plates, 0.5 mL/well. Cells were transfected immediately with 50 μL of DODAC:DOPE/pCMVβ, or after 48 h mitogenic stimulation with Concanavalin A (1, 2.5 and 5 μg/mL; Sigma) and lipopolysaccharide (2.5 and 5 μg/mL; Sigma). Cells were incubated for 48 h in the presence of the transfection agent, after which time they were stained for β-gal expression as described above. Separate wells were set up for appropriate controls: no treatment, naked pCMVβ, or DODAC:DOPE in the absence of plasmid DNA.

8.4 Results

Transfection of primary splenocytes, thymocytes and bone marrow cells using the cationic liposomes resulted in a low level of β-gal positive cells (<5%). The levels achieved were significantly above those obtained with the naked DNA control, which had few β-gal positive cells (<0.01%) and comparable to the untreated cells. In some experiments, non-adherent splenocytes were separated from adherent cells prior to fixing and staining for β-gal activity. In at least two experiments, >80% of the adherent splenocytes (morphologically resembling macrophages) stained positively for β-gal activity. Few cells in the non-adherent cell fraction stained for β-gal activity. These cells, being small and round, resembled lymphocytes. Both non-stimulated and stimulated cells gave similar low levels of transfection. The expression levels from the pCMVβ expression vector in primary cells is estimated to be fairly low (based on the time required for cells to turn blue). β-gal assays are relatively insensitive, requiring several hundred copies per cell in order to detect a blue cell. Therefore, at least for primary cells, stronger mammalian expression vectors are required to facilitate measurement of β-gal reporter gene expression. Immunological characterization of the cells is required to identify the cells that are being transfected. This in vitro assay employing primary mixed cell cultures derived from whole organs is very useful for optimizing these fusogenic cationic liposomal systems for gene transfer to macrophages and CD4⁺ T lymphocytes, the target cells for an anti-HIV gene therapy program.

EXAMPLE 9

This example provides a comparison of the transfection properties of a DODAC:DOPE lipid mixture and a DOTMA:DOPE lipid mixture.

When cationic lipids are used to mediate the transcellular delivery of genetic constructs in vivo, the standard procedure involves adding preformed vesicles to a DNA solution and subsequently injecting the vesicle/DNA complex into the animal. Below is a comparison of a DODAC:DOPE lipid mixture to a DOTMA:DOPE (LIPOFECTIN®) lipid mixture.

9.1 Cationic lipids

The monocationic lipids, dioleyldimethylammonium chloride (DODAC, mw=584.6 g/mol) and 1,2-dioleyloxy-3-(N,N,N-trimethylamino)propane chloride (DOTMA, mw=670 g/mol) were synthesized by the methods described herein and by an adaptation of the method in U.S. Pat. No. 4,946,787. Briefly, in the method described in U.S. Pat. No. 4,946,787, methyl chloride was replaced with methyl iodide in the presence of excess aqueous sodium hydroxide. The iodide ion was removed from the product and exchanged with chloride ion by washing the product with HCl, followed by brine. DOPE was purchased from Avanti Polar Lipids and from Northern Lipids.

9.2 Vesicle formation

A thin lipid film was formed by first mixing the lipids in $CHCl_3$ and then removing the solvent under a stream of nitrogen gas. The film was then left under vacuum for 2 hr to remove residual organic solvent. A multilamellar vesicle suspension was formed by hydrating the lipid film in distilled water. After freeze-thawing the MLV suspension 5 times using liquid nitrogen and 60° C. water cycles, the vesicles were extruded through 2 stacked 100 nm diameter pore sized Nuclepore filters.

9.3 Formation of cationic lipid/DNA complex

The cationic vesicles and DNA were diluted to equal volumes (600 βL) in 5% glucose (final concentration). The vesicles and DNA were then rapidly mixed together and left for a minimum of 30 minutes before injection, but used within 3 hr of mixing. Use of glass test tubes was avoided as DNA sticks to glass. When more than 1.2 mL of the complex was needed, the complexes were made in 1.2 mL aliquots and pooled as adding the vesicles and DNA together in large volumes result in a particulate solution due to uneven mixing. The complexes were typically made at 50 μg DNA/400 μL.

9.4 Charge ratio calculations

The physical properties of the complexes (fusion and DNA condensation) as well as the in vitro transfection data is expressed in terms of (±) charge ratios. For example, the molecular weight of DODAC:DOPE (1:1, mol ratio) is 664 g/mol and the average molecular weight of a DNA nucleotide is 325 g/mol. As one DNA nucleotide has one negative charge, complexes formed with 50 μg DNA and 0.92 μmol or 0.61 mg DODAC:DOPE is denoted a charge ratio of 3.

9.5 CAT assay pCMV₄CAT (a gift from Dr. Hugh O'Brodovitch at The Sick Children's Hospital of Toronto, Toronto, Ontario, Canada) was used as the reporter gene in these studies. A radioactive phase partition CAT enzyme assay (as described below) was used to determine the degree of transfection.

Materials:

250 mM Tris HCl/5 mM EDTA buffer pH 7.8; Leupeptin and aprothinin (from Boerhinger) stock solutions (0.1%) for each weigh out 0.0025 g and add both to 2.5 mL of distilled water. Mix, aliquot and store at −20° C. for up to 6 months or store 1 week at 4° C.; Phenylmethylsulfonylfluoride stock solution (PMSF) 10 mg/mL, prepared from 0.05 g of PMSF and 5 mL of isopropanol (Store in the dark at room temperature for up to 1 year); Complete homogenation buffer (from Tris HCl/EDTA buffer (100 mL), PMSF stock (350 μL, final concentration of 35 μg/mL), and leupeptin/aprotinin stock (50 μL, final concentration of 0.5 μL/mL)); BSA buffer, prepared from complete homogenation buffer+2 mg/mL BSA, fraction V; n-butyryl co-enzyme A (Sigma B1508 lyophilized powder diluted to 5 mg/mL and stored at -20° C. in small aliquots to avoid excessive freeze-thawings); CAT enzyme (Sigma C8413 chloramphenicol acetyltransferase); $^{14}$C-chloramphenicol (NEN NEC-408A chloramphenicol, D-threo-[dichloroacetyl-1,2-$^{14}$C]-CAT assay grade (TLC based), stored at 4° C. and diluted 1:10 in BSA buffer just prior to use); mixed xylenes (Aldrich); paraoxon (diethyl-n-nitrophenyl phosphate, from Sigma is a liquid with 90% purity) stock solution is prepared by diluting the original liquid 1:80 in isopropanol (Note: To achieve a final paraoxon concentration of 5 μM in a 130 μL of reaction mixture, a further 1:200 dilution in homogenization buffer is made and 3.3 μL of this 0.8 mM paraoxon solution is added to the reaction mixture); BCA protein reagent.

Method:

A. Tissue homogenization procedure:

Mice are euthanized by placing them in a container flooded with carbon dioxide. The appropriate tissues are collected and kept on ice or frozen in liquid nitrogen. Homogenization buffer is added to the tissues and the mixture is homogenized to form a 25% (0.25 g/mL) solution with spleen and liver tissues or a 40% solution with lung tissue. The mixtures are immediately transferred to microcentrifuge tubes and frozen in liquid nitrogen. With liver samples, it's easier to homogenize a 50% solution then dilute an aliquot 2 times to obtain a 25% solution. A cell extract is formed from the tissue homogenate by freeze-thawing 3 times using liquid nitrogen and 37° C. water cycles. The resulting extract is centrifuged at 10,000 rpm (microcentrifuge high/full speed) for 10 minutes to pellet the cell debris. The supernatant is transferred to a new microcentrifuge tube and heat inactivated for 15 minutes at 65° C. The supernatent is then centrifuged as above (10,000 rpm for 10 min) and transferred to a new microcentrifuge tube and stored at −70° C. until ready to assay for CAT activity.

B. Protein assay of cell extract

A protein assay is needed to normalize the amount of CAT activity. Using the BCA protein assay and BSA as the standard, typical protein concentrations of the tissue extracts are 5–10 mg/mL for the liver and spleen and 10 mg/mL for the lungs. Thus, lung extracts are diluted 20 times and liver and spleen extracts are diluted 15 times in distilled water. BSA standards are prepared with concentrations of 0.2, 0.3, 0.4, 0.5, 0.6, 0.7 and 0.8 mg/mL. Ten μL of the standards or samples are added to 48 well plates (in duplicate or triplicate) and 190 μL of the BCA reagent is added to the wells. After 20 minutes the absorbance is read at 540 nm using a plate reader.

C. CAT standard curve

The CAT enzyme supplied by Sigma has an activity of 110 units per 10 μl (one unit of CAT will convert 1 nanomole of chloramphenicol and acetyl-CoA to chloramphenicol 3-acetate and CoA per minute at pH7.8 at 25° C.).

| standard # | [CAT] mUnits/10 μL | ng/10 μL | BSA buffer (μL) | dilution (μL) |
|---|---|---|---|---|
| 1 | 100 | 1 | 2200 | 2 of CAT stock |
| 2 | 5.0 | 0.050 | 950 | 50 of (1) |
| 3 | 3.0 | 0.030 | 100 | 150 of (2) |
| 4 | 2.0 | 0.020 | 150 | 100 of (2) |
| 5 | 1.5 | 0.015 | 175 | 75 of (2) |
| 6 | 1.0 | 0.010 | 200 | 50 of (2) |
| 7 | 0.5 | 0.005 | 225 | 25 of (2) |
| 8 | 0.1 | 0.001 | 100 | 25 of (7) |

For the CAT assay, an incubation mixture is prepared by combining 25 μL of n-butyryl CoA, 50 μL of diluted $^{14}$C-chloramphenicol, 55 μL BSA buffer or control tissue extract, and 3.3 μL of 0.8 mM paraoxon. The standard curve is generated by adding an additional 10 μL of the various CAT standards to the incubation mixture. The mixtures are incubated at 37° C. for 2 h. Xylene (300 μL) is added and the mixture is vortexed for 30 sec, then centrifuged for 3 min at 10,000 rpm. The upper xylene phase is removed to a fresh microcentrifuge tube containing 750 μL homogenization buffer and vortexed and centrifuged as above. An aliquot (125 μL) of the upper phase is removed to a scintillation vial and counted.

9.6 Results

Following intravenous administration, the in vivo transfection activity of cationic vesicle/DNA complexes was assessed. DODAC:DOPE (1:1 mol ratio), DODAC:DOPE (1:1 mol ratio) with 2% PEG-Cer-$C_{20}$, DODAC:DOPE (3:7) and DOTMA:DOPE were all found to mediate transfection at a charge ratio of 2.5. CAT activity was determined 2–3 days after injection. Additionally, complexes made at charge ratios of 2.5 and 3.0 were all active but those prepared at a charge ratio of 0.5 were not active.

With regard to the amounts of DNA necessary, 25 μg DNA was found to give measurable CAT activity (500–2000 dpms above background in the spleen). In terms of CAT activity per mg tissue, the organs which show transfection activity include the spleen>>lung and heart>liver. No activity was detected in the blood after 2 days. Paraoxan (1 μM) must be included in the liver tissue extract to allow measurement of CAT activity due to high levels of other competing acetylating enzymes.

Figure 8:
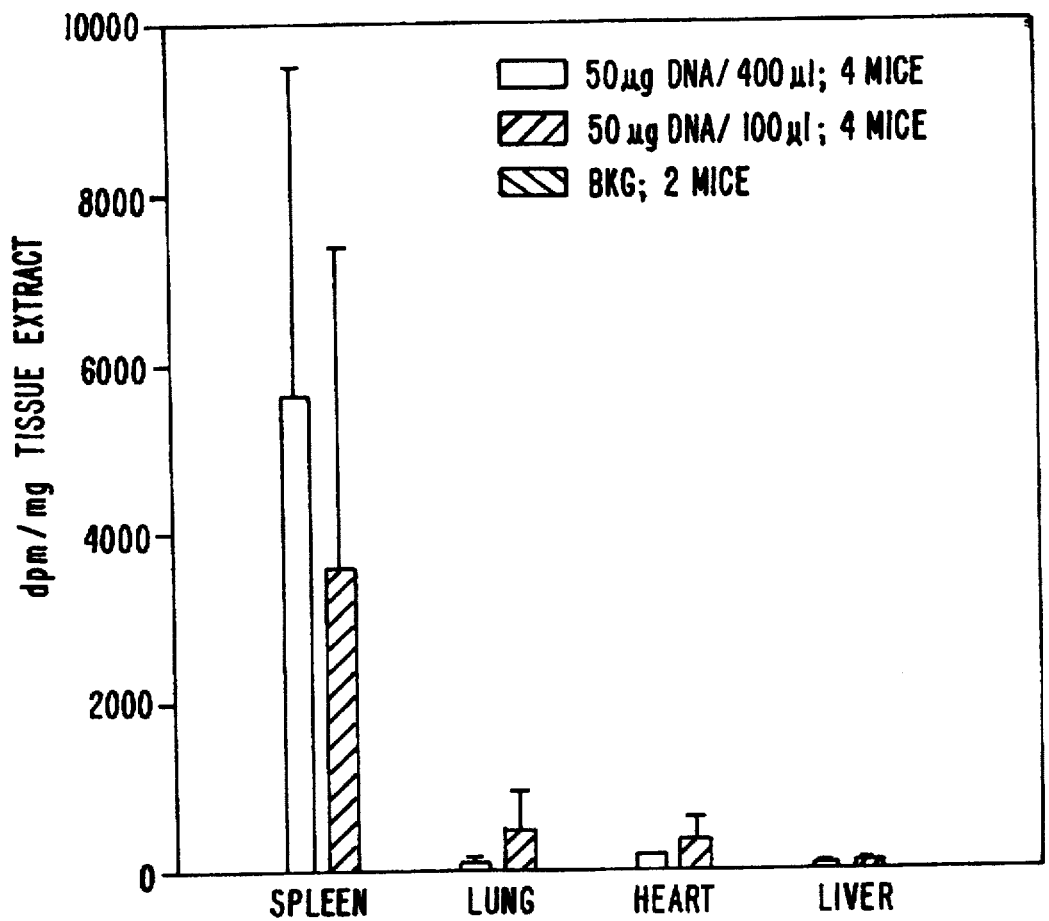
FIG. 8 illustrates the transfection efficiencies of DODAC:DOPE complexes with ICR mice.

Typically, complexes have been made at a charge ratio of 3 and containing 50 μg DNA in a 350–400 μL volume. At this concentration, the complexes are 200–400 nm in diameter. When the complexes are made at higher concentrations, a particulate (>1 μm dia.) solution forms. However, addition of plasma disrupts these large aggregates and forms particles that are transfectionally active in vitro. Injection of either a particulate solution (50 μg DNA/100 μL) or a more dilute solution (50 μg DNA/400 μL) was found to give comparable CAT activity in vivo (see FIG. 8), suggesting that the large precipitates have time to disaggregate in the circulation.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A pharmaceutical composition for introducing a polyanion into a cell, said composition being a liposome formulation and comprising a cationic compound of formula (I)

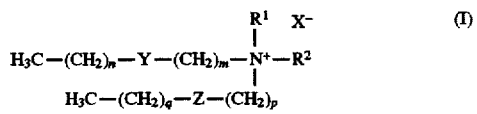

wherein $R^1$ and $R^2$ are each independently $C_1$ to $C_3$ alkyl;

Y and Z are each independently members selected from the group consisting of —$CH_2CH_2CH_2CH_2CH_2$—, —CH=CHCH$_2$CH$_2$CH$_2$—, —CH$_2$CH=CHCH$_2$CH$_2$—,
—CH$_2$CH$_2$CH=CHCH$_2$—,
—CH$_2$CH$_2$CH$_2$CH=CH—,
—CH=CHCH=CHCH$_2$—,
—CH=CHCH$_2$CH=CH—, and
—CH$_2$CH=CHCH=CH—, with the proviso that Y and Z are not both —CH$_2$CH$_2$CH$_2$CH$_2$CH$_2$—;

n and q are independently integers of from 3 to 7; and m and p are independently integers of from 4 to 9, with the proviso that the sums n+m and q+p are each integers of from 10 to 14; and X$^-$ is a pharmaceutically acceptable anion selected from the group consisting of chloride, bromide, fluoride, iodide, nitrate, sulfate, phosphate, acetate, benzoate, citrate, glutamate, and lactate;

at least one neutral lipid selected from the group consisting of diacylphosphatidylcholine, diacylphosphatidylethanolamine, ceramide and sphingomyelin; and a pharmaceutically acceptable carrier.

2. A composition in accordance with claim 1, wherein said neutral lipid is 1,2-sn-dioleoylphosphatidylethanolamine.

3. A composition in accordance with claim 1, wherein R$^1$ and R$^2$ are methyl, Y and Z are independently members selected from the group consisting of —CH=CHCH$_2$CH$_2$CH$_2$—, —CH$_2$CH=CHCH$_2$CH$_2$—, —CH$_2$CH$_2$CH=CHCH$_2$— and —CH$_2$CH$_2$CH$_2$CH=CH—.

4. A composition in accordance with claim 1, wherein R$^1$ and R$^2$ are methyl, Y and Z are both —CH=CHCH$_2$CH$_2$CH$_2$—, n and q are both 7, and m and p are both 5.

5. A composition in accordance with claim 1, wherein X$^-$ is Cl$^-$.

6. A composition in accordance with claim 1, wherein said cationic compound is DODAC and said neutral lipid is 1,2-sn-dioleoylphosphatidylethanolamine.

* * * * *

UNITED STATES PATENT AND TRADEMARK OFFICE
CERTIFICATE OF CORRECTION

PATENT NO. : 5,785,992
DATED : July 28, 1998
INVENTOR(S) : Steven Michial Ansell; Barbara Mul; Michael Hope It is certified that error appears in the above-identified patent and that said Letters Patent is hereby corrected as shown below:

Column 1, after "[22] Filed: Sep. 29, 1995," the following data should be inserted:

Related U.S. Application Data

[60] Continuation-in-part of Ser. No. 08/316,399, Sep. 30, 1994 and 08/442,267, May 16, 1995

Signed and Sealed this

Twelfth Day of September, 2000

Attest:

Q. TODD DICKINSON

*Attesting Officer*     *Director of Patents and Trademarks*